US008362035B2

(12) United States Patent
Berkenbusch et al.

(10) Patent No.: US 8,362,035 B2
(45) Date of Patent: *Jan. 29, 2013

(54) CRYSTALLINE FORMS OF A POTENT HCV INHIBITOR

(75) Inventors: Thilo Berkenbusch, Worms (DE); Carl Alan Busacca, Poughkeepsie, NY (US); Burkhard Jaeger, Bingen (DE); Richard J. Varsolona, Scotch Plains, NJ (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/541,158

(22) Filed: Jul. 3, 2012

(65) Prior Publication Data

US 2012/0270775 A1    Oct. 25, 2012

Related U.S. Application Data

(63) Continuation of application No. 12/559,927, filed on Sep. 15, 2009, now Pat. No. 8,232,293.

(60) Provisional application No. 61/150,826, filed on Mar. 9, 2009, provisional application No. 61/097,291, filed on Sep. 16, 2008.

(51) Int. Cl.
*A61K 31/4709* (2006.01)
*A61K 31/427* (2006.01)
*A61K 31/4025* (2006.01)
*C07D 215/233* (2006.01)
*C07D 417/14* (2006.01)
*C07D 207/12* (2006.01)

(52) U.S. Cl. ........ 514/312; 514/370; 514/422; 546/153; 548/181; 548/519

(58) Field of Classification Search .................. 514/312, 514/370, 422; 546/153; 548/181, 519
See application file for complete search history.

(56) References Cited

U.S. PATENT DOCUMENTS

| 6,323,180 | B1 | 11/2001 | Llinas-Brunet et al. |
| RE40,525 | E | 9/2008 | Llinas-Brunet et al. |
| 7,514,557 | B2 * | 4/2009 | Busacca et al. ............... 546/154 |
| 7,585,845 | B2 | 9/2009 | Llinas-Brunet et al. |
| 2005/0020503 | A1 | 1/2005 | Llinas-Brunet et al. |
| 2010/0093792 | A1 | 4/2010 | Berkenbusch et al. |
| 2012/0059033 | A1 | 3/2012 | Yang et al. |

FOREIGN PATENT DOCUMENTS

| WO | 0009543 A2 | 2/2000 |
| WO | 2004087741 A1 | 10/2004 |
| WO | 2004103996 A1 | 12/2004 |
| WO | 2010033444 A1 | 3/2010 |
| WO | 2011112761 A1 | 9/2011 |

OTHER PUBLICATIONS

Guillory, J. K., "Methods Employed to Obtain Amorphous Materials—Lyophilization", Polymorphism in Pharmaceutical Solids (ed. H. G. Bittain), Chapter 5, Section IV, pp. 213-217, Marcel Dekker, New York, 1999.
International Search report, Form PCT/ISA/220, and Written Opinion, Form PCT/ISA/210, for application PCT/US2009/056772, date of mailing Nov. 23, 2009.
Caira et al., Crystalline Polymorphism of Organic Compounds, Topics in Current Chemistry, 1998, vol. 198, pp. 163-208, ISSN: 0340-1022.

* cited by examiner

*Primary Examiner* — Joseph Kosack
(74) *Attorney, Agent, or Firm* — Michael P. Morris; Philip I. Datlow

(57) ABSTRACT

This invention relates to novel crystalline forms of the following Compound (1), and the sodium salt thereof, and methods for the preparation thereof, pharmaceutical compositions thereof, and their use in the treatment of Hepatitis C Viral (HCV) infection:

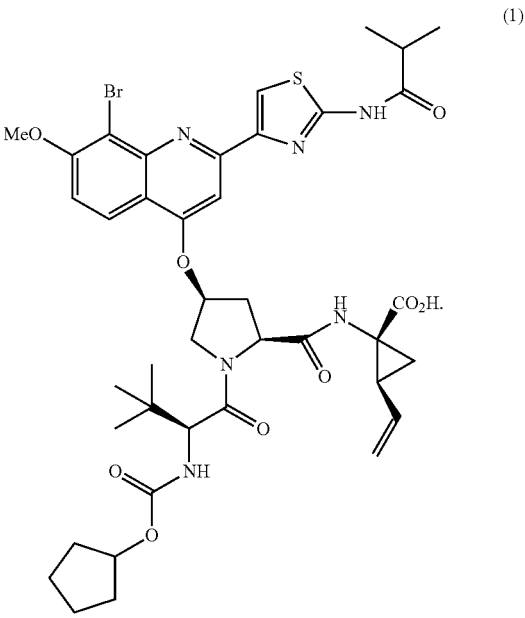

10 Claims, 5 Drawing Sheets

CRYSTALLINE FORMS OF A POTENT HCV INHIBITOR

FIELD OF THE INVENTION

This invention relates to novel crystalline forms of Compound (1) and the sodium salt of Compound (1) as described herein, methods for the preparation thereof, pharmaceutical compositions thereof, and their use in the treatment of Hepatitis C Viral (HCV) infection.

BACKGROUND OF THE INVENTION

The following Compound (1):

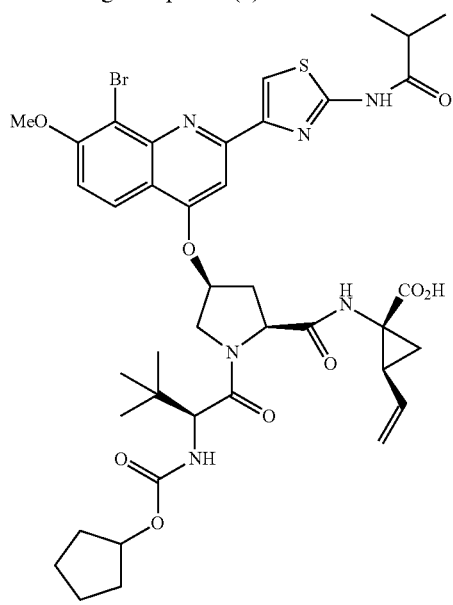

(1)

is known as a selective and potent inhibitor of the HCV NS3 serine protease. Compound (1) falls within the scope of the acyclic peptide series of HCV inhibitors disclosed in U.S. Pat. Nos. 6,323,180, 7,514,557 and 7,585,845. Compound (1) is disclosed specifically as Compound #1055 in U.S. Pat. No. 7,585,845, and as Compound #1008 in U.S. Pat. No. 7,514,557. Compound (1) can be prepared according to the general procedures found in the above-cited references, which are herein incorporated by reference.

Compound (1) may also be known by the following alternate depiction of its chemical structure, which is equivalent to the above-described structure:

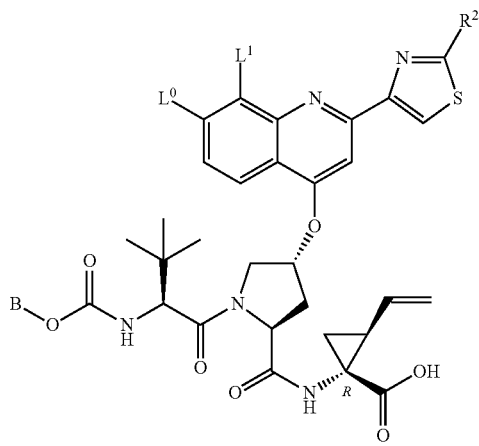

wherein B is

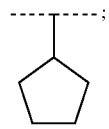

$L^0$ is MeO—; $L^1$ is Br; and $R^2$ is

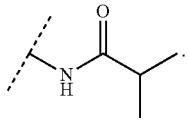

When synthesized according to the general procedures set forth in the above-cited references, Compound (1) is prepared as an amorphous solid which is a form that is generally less suitable for full-scale pharmaceutical processing. Thus, there is a need to produce Compound (1) in a crystalline form to enable formulations to meet exacting pharmaceutical requirements and specifications. Furthermore, the process by which Compound (1) is produced needs to be one which is amenable to large-scale production. Additionally, it is desirable that the product should be in a form that is readily filterable and easily dried. Finally, it is economically desirable that the product be stable for extended periods of time without the need for specialized storage conditions.

SUMMARY OF THE INVENTION

We have now surprisingly and unexpectedly found for the first time that Compound (1) can be prepared in crystalline form and also in the form of its sodium salt, and more preferably, the crystalline sodium salt form. Thus, the present invention provides Compound (1) in crystalline form, which in one embodiment is the new crystalline polymorph designated herein as Type A, and also in the form of a novel crystalline sodium salt of Compound (1). These novel crystalline forms overcome the pharmaceutical processing difficulties inherent in the use of an amorphous form and the sodium salt form, in particular, has other properties making it particularly advantageous in pharmaceutical formulation processing as will be described in detail below.

In one embodiment, the present invention is directed to Compound (1) in crystalline form. In a more specific embodiment, the present inventors have discovered a novel crystalline polymorph of Compound (1), referred to hereinafter as "Type A".

Type A exhibits a characteristic X-ray powder diffraction (XRPD) pattern with characteristic peaks expressed in degrees 2θ (±0.2 degrees 2θ) at 4.8, 6.8, 9.6, 13.6, 17.3, 19.8 and 24.5 measured using CuKα radiation.

Another embodiment is directed to the sodium salt of Compound (1), which sodium salt can be prepared in crystalline form. The crystalline sodium salt of Compound (1) exhibits a characteristic X-ray powder diffraction (XRPD) pattern with characteristic peaks expressed in degrees 2θ (±0.2 degrees 2θ) at 5.4, 6.5, 8.7, 10.1, 11.9, 13.0, 18.2, 20.2 and 24.7 measured using CuKα radiation.

Yet another embodiment is directed to a pharmaceutical composition comprising Type A or the sodium salt of Compound (1), or mixtures thereof, and at least one pharmaceutically acceptable carrier or diluent.

Yet another embodiment is directed to a method of treating HCV infection in a mammal comprising administering to said mammal a therapeutically effective amount of Type A or the sodium salt of Compound (1), or mixtures thereof.

DETAILED DESCRIPTION OF THE INVENTION

Definitions

Terms not specifically defined herein should be given the meanings that would be given to them by one of skill in the art in light of the disclosure and the context. As used throughout the present application, however, unless specified to the contrary, the following terms have the meaning indicated:

The term "Type A" means a crystalline polymorph of Compound (1) that has an X-ray powder diffraction pattern having at least a characteristic peak at 9.6 degrees 2θ (±0.2 degrees 2θ) when measured using CuKα radiation. This characteristic peak is believed to distinguish Type A from other crystalline forms of Compound (1).

The term "about" means within 5%, and more preferably within 1% of a given value or range. For example, "about 3.7%" means from 3.5 to 3.9%, preferably from 3.66 to 3.74%. When the term "about" is associated with a range of values, e.g., "about X % to Y %", the term "about" is intended to modify both the lower (X) and upper (Y) values of the recited range. For example, "about 20% to 40%" is equivalent to "about 20% to about 40%".

The term "pharmaceutically acceptable" with respect to a substance as used herein means that substance which is, within the scope of sound medical judgment, suitable for use in contact with the tissues of humans and lower animals without undue toxicity, irritation, allergic response, and the like, commensurate with a reasonable benefit/risk ratio, and effective for the intended use when the substance is used in a pharmaceutical composition.

The term "treating" with respect to the treatment of a disease-state in a patient include
 (i) inhibiting or ameliorating the disease-state in a patient, e.g., arresting or slowing its development; or
 (ii) relieving the disease-state in a patient, i.e., causing regression or cure of the disease-state. In the case of HCV, treatment includes reducing the level of HCV viral load in a patient.

Crystalline Compound (1)

The Compound (1) has been isolated as a crystalline polymorphic form designated herein as "Type A". In general, Type A exhibits a characteristic X-ray powder diffraction ("XRPD") pattern with peaks expressed in degrees 2θ (±0.2 degrees 2θ) at 4.8, 6.8, 9.6, 13.6, 17.3, 19.8 and 24.5.

Figure 1:
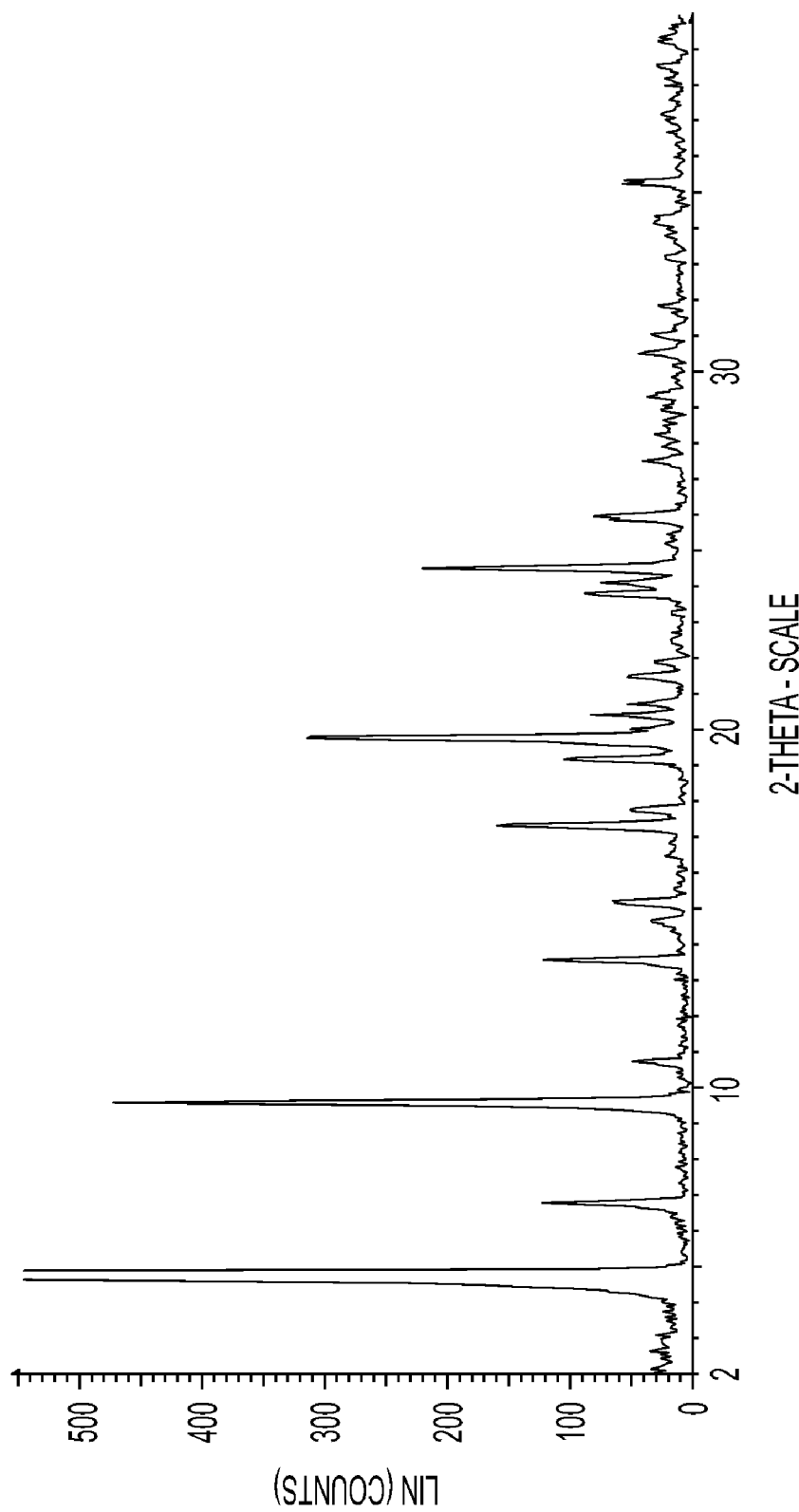
FIG. 1 is a characteristic X-ray Powder Diffraction (XRPD) pattern for Type A.

The XRPD pattern of Type A is shown in FIG. 1. The characteristic peak positions and relative intensities for the XRPD pattern in FIG. 1 is shown in Table 1 below.

TABLE 1

Compound (1)
Type A

| Angle 2-Theta ° | Rel. Intensity % |
|---|---|
| 4.8 | 100 |
| 6.8 | 6 |
| 9.6 | 24 |
| 13.6 | 6 |
| 17.3 | 8 |
| 19.8 | 16 |
| 24.5 | 11 |

Figure 2:
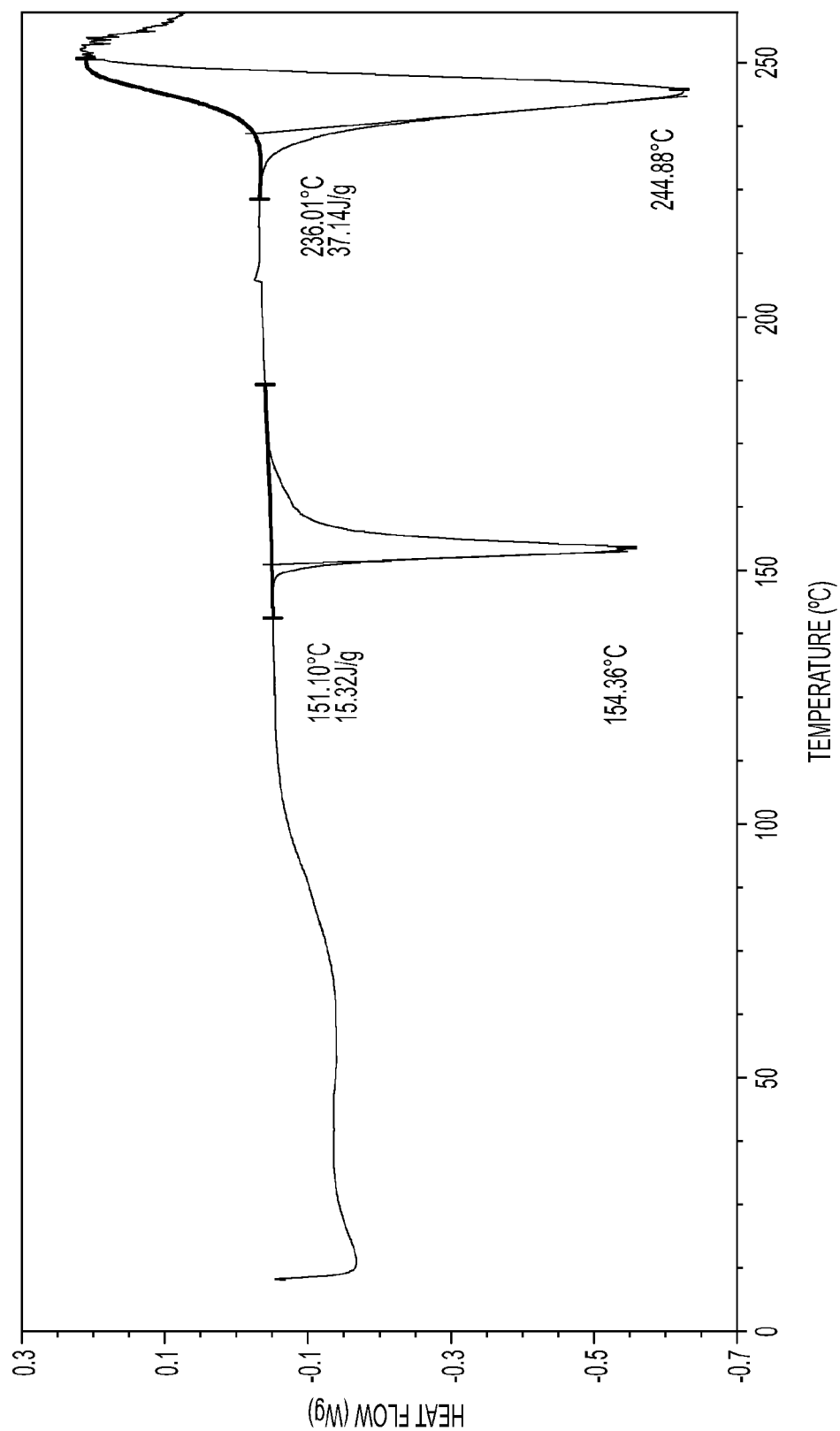
FIG. 2 is the DSC thermal curve for Type A crystals where the DSC is performed at a heating rate of 10° C. per minute in a crimped cup.

FIG. 2 shows the Differential Scanning Calorimetry (DSC) thermal curve for Type A crystals where the DSC is performed at a heating rate of 10° C. per minute in a crimped cup.

In one general embodiment, the present invention is directed to Compound (1) in crystalline form.

Another more specific embodiment is directed to a crystalline polymorph of Compound (1) that has at least the following characteristic: an X-ray powder diffraction pattern comprising a peak at 9.6 degrees 2θ (±0.2 degrees 2θ) when measured using CuKα radiation.

Another embodiment is directed to a crystalline polymorph of Compound (1) having an XRPD pattern comprising a peak at 9.6 degrees 2θ (±0.2 degrees 2θ) as described above and further comprising a peak at 19.8 degrees 2θ (±0.2 degrees 2θ) when measured using CuKα radiation.

Another embodiment is directed to a crystalline polymorph of Compound (1) having an XRPD pattern comprising a peak at 9.6 degrees 2θ (±0.2 degrees 2θ) as described above and further comprising peaks at 4.8 and 19.8 degrees 2θ (±0.2 degrees 2θ) when measured using CuKα radiation.

Another embodiment is directed to a crystalline polymorph of Compound (1) having an XRPD pattern comprising a peak at 9.6 degrees 2θ (±0.2 degrees 2θ) as described above and further comprising peaks at 4.8, 6.8, 13.6, 17.3, 19.8 and 24.5 degrees 2θ (±0.2 degrees 2θ) when measured using CuKα radiation.

Another embodiment is directed to a crystalline polymorph of Compound (1) exhibiting an XRPD pattern substantially the same as that shown in FIG. 1.

Another embodiment is directed to a crystalline polymorph of Compound (1) having an XRPD pattern comprising a peak at 9.6 degrees 2θ (±0.2 degrees 2θ) as described above and also exhibiting a DSC thermal curve substantially the same as that shown in FIG. 2 at a heating rate of 10° C. per minute in a crimped cup.

Another embodiment is directed to a quantity of Compound (1) wherein at least 50%, preferably at least 75%, more preferably at least 95%, more preferably at least 99%, of said substance is present in crystalline form, for example, in the form of the Type A crystalline polymorph as characterized by any of the abovementioned XRPD-defined embodiments. The presence of such amounts of Types A in a quantity of Compound (1) is typically measurable using XRPD analysis of the compound.

An additional embodiment is directed to a pharmaceutical composition comprising Compound (1) and a pharmaceutically acceptable carrier or diluent, wherein at least 50%, preferably at least 75%, more preferably at least 95%, more preferably at least 99%, of the Compound (1) in the composition is present in crystalline form, for example, in the form of the Type A crystalline polymorph as characterized by any of the abovementioned XRPD-defined embodiments.

The present invention provides a process for the preparation of Type A which comprises crystallizing Compound (1) from a solution in solvents under conditions which yield Type A. The precise conditions under which Type A is formed may be empirically determined and it is only possible to give methods which have been found to be suitable in practice.

It has been found that Type A of Compound (1) may be prepared by a process comprising the following steps, which process is also an embodiment of the present invention:
 (i) dissolving Compound (1) in an aliphatic alcohol solvent, optionally containing water as a co-solvent, by heating the mixture to a temperature of about 65 to 75° C. to obtain a solution;
 (ii) adding water to the solution obtained in step (i) while maintaining the solution at a temperature of about 70 to 75° C. to obtain a slurry;
 (iii) cooling the slurry obtained in step (ii) to obtain solid material;
 (iv) collecting the solid material of step (iii) and drying said material at a temperature of about 65 to 80° C. to obtain Type A of Compound (1).

Aliphatic alcohols that may be employed in this process include, for example, ethanol (e.g., denatured, 200 proof or 100% pure), 1-propanol, 2-propanol, 1-butanol, iso-butyl alcohol and iso-pentyl alcohol, preferably ethanol. The resulting crystals of Type A may be recovered by any conventional methods known in the art.

In the final step (iv), the resulting solids obtained in step (iii) may be collected and dried at high temperature using conventional collection and high-temperature drying techniques, for example, filtration and vacuum oven.

In one preferred embodiment, amorphous Compound (1) is dissolved in an aliphatic alcohol solvent (e.g., ethanol), containing up to about 10% v/v water as co-solvent, by stirring and heating the mixture to a temperature of about 72 to 74° C. until Compound (1) completely dissolves. A separate water addition solution is prepared containing water and up to about 10% v/v aliphatic alcohol (e.g., ethanol), and this water addition solution is added approximately linearly over time to the Compound (1) solution while maintaining the mixture at a temperature of about 72 to 74° C. Type A of Compound (1) begins to crystallize during the addition of the water solution. The resulting crystal slurry is cooled and stirred, and the crystals are then filtered, washed and dried at a temperature of about 65 to 75° C. using conventional techniques.

The process steps may of course be facilitated by conventional agitation techniques, e.g., stirring, and other conventional techniques as would be well understood for facilitation the process.

Sodium Salt of Compound (1)

The sodium salt of the Compound of formula (1) has been found to be especially suitable for pharmaceutical processing due to the fact that it can be prepared as a stable crystalline form. In general, the crystalline sodium salt of Compound (1) exhibits a characteristic X-ray powder diffraction (XRPD) pattern with characteristic peaks expressed in degrees 2θ (±0.2 degrees 2θ) at 5.4, 6.5, 8.7, 10.1, 11.9, 13.0, 18.2, 20.2, and 24.7.

Figure 3:
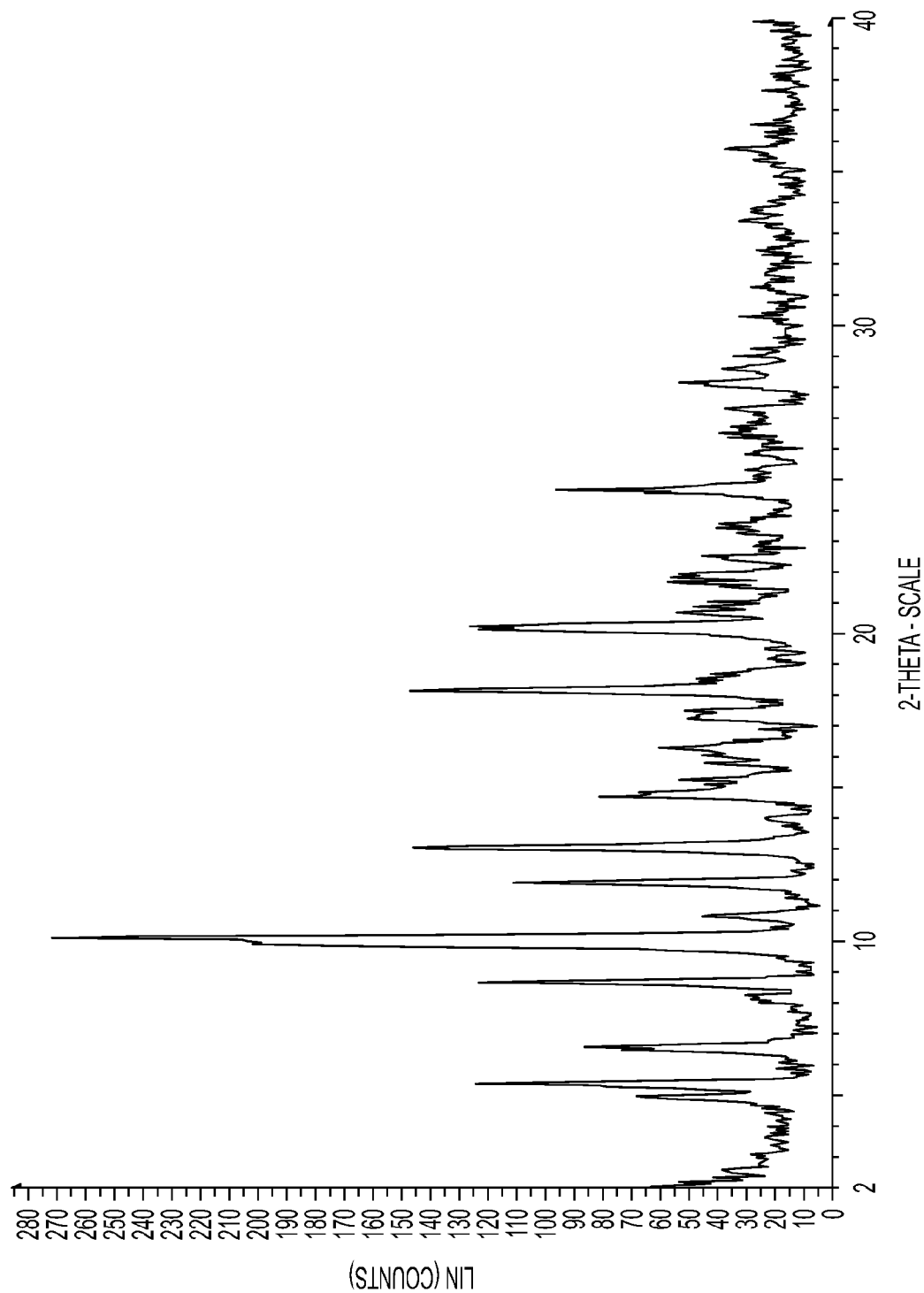
FIG. 3 is a characteristic X-ray Powder Diffraction (XRPD) pattern for the crystalline sodium salt of Compound (1).

The XRPD pattern of the crystalline sodium salt of Compound (1) is shown in FIG. 3. The characteristic peak positions and relative intensities for the XRPD pattern in FIG. 3 is shown in Table 2 below.

TABLE 2

| Compound (1) Crystalline Na Salt | |
|---|---|
| Angle 2-Theta ° | Rel. Intensity % |
| 5.4 | 42 |
| 6.5 | 29 |
| 8.7 | 43 |
| 10.1 | 100 |
| 11.9 | 39 |
| 13.0 | 52 |
| 18.2 | 51 |
| 20.2 | 42 |
| 24.7 | 30 |

Figure 4:
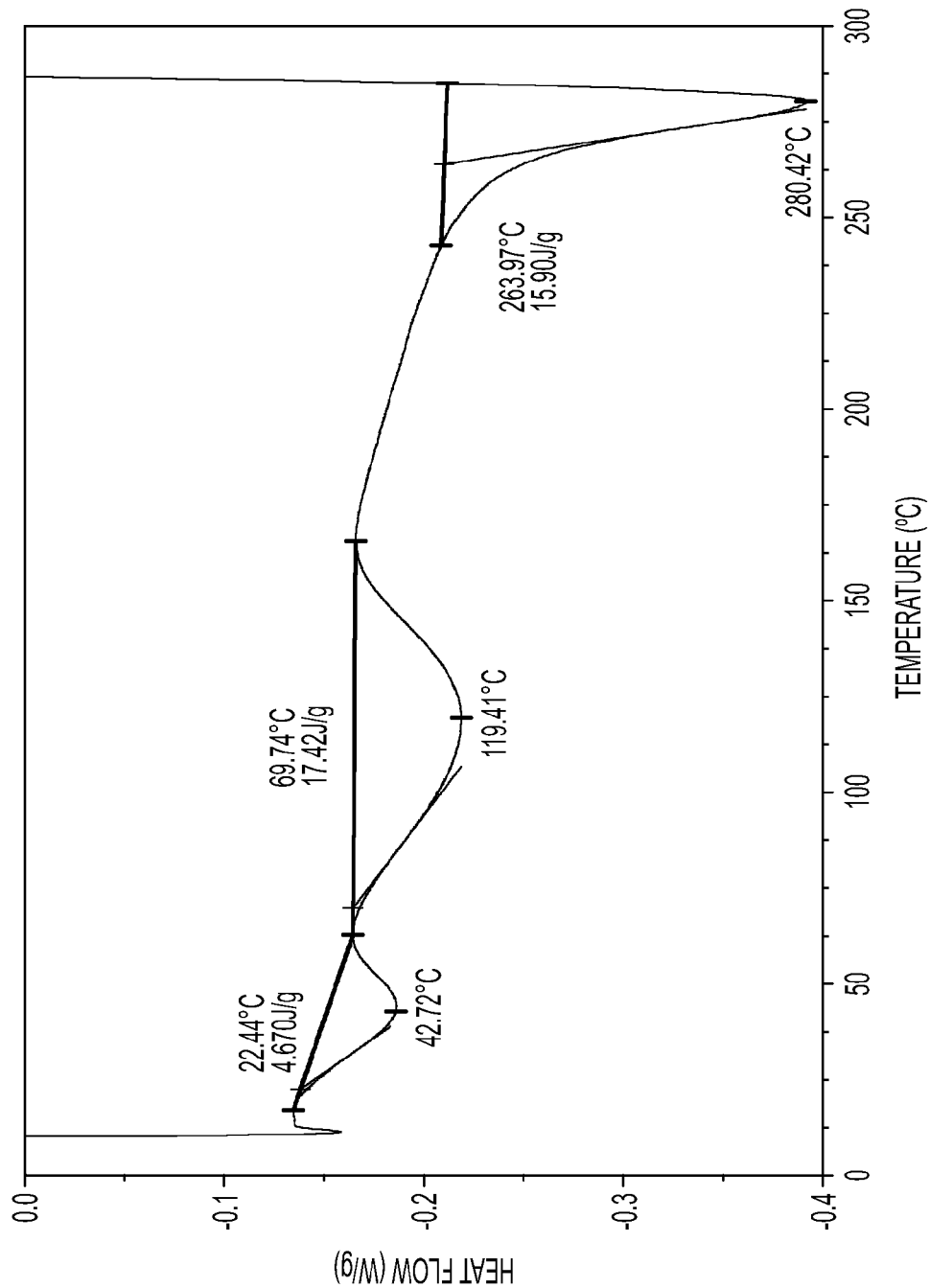
FIG. 4 is the DSC thermal curve for crystals of the crystalline sodium salt of Compound (1) where the DSC is performed at a heating rate of 10° C. per minute in a open cup.

FIG. 4 shows the Differential Scanning Calorimetry (DSC) thermal curve for the crystalline sodium salt of Compound (1) crystals where the DSC is performed at a heating rate of 10° C. per minute in a open cup.

The sodium salt form has been unexpectedly found to have unique properties making it particularly advantageous in pharmaceutical formulation processing. In particular, the sodium salt form has certain properties making it particularly suitable for formulating in a Lipid-Based Drug Delivery System (LBDDS).

First, the sodium salt form was unexpectedly found to have much improved solubility in excipients commonly used for LBDDS formulation including, for example, propylene glycol and ethanol. The table below provides data demonstrating the much improved solubility of the sodium salt form of Compound (1) as compared to the Type A form of Compound (1) in particular excipients:

Comparison of Solubility of Compound (1) Na salt vs. Compound (1) Type A in various excipients

| Excipient | Compound (1) Na salt (mg/mL) | Type A of Compound (1) (mg/mL) |
|---|---|---|
| PEG 400 | 233.6 ± 34 | 136.8 ± 3.2 |
| Propylene Glycol | >468 | 1.3 ± <0.01 |
| Ethanol | 187.0 ± 23.9 | 0.9 ± 0.1 |
| Capmul PG8 | <169 | 172.6 ± 8.3 |
| Capmul MCM | 262.5 ± 2.6 | 220.6 ± 7.4 |
| Transcutol P | 430.6 ± 14.7 | 24.3 ± 0.3 |
| Labrasol | 174.6 ± 11.8 | 146.7 ± 5.1 |

The much improved solubility of the sodium salt form in propylene glycol and ethanol makes this form particularly suited to the development of an LBDDS formulation employing one or more of these common excipients.

Figure 5:
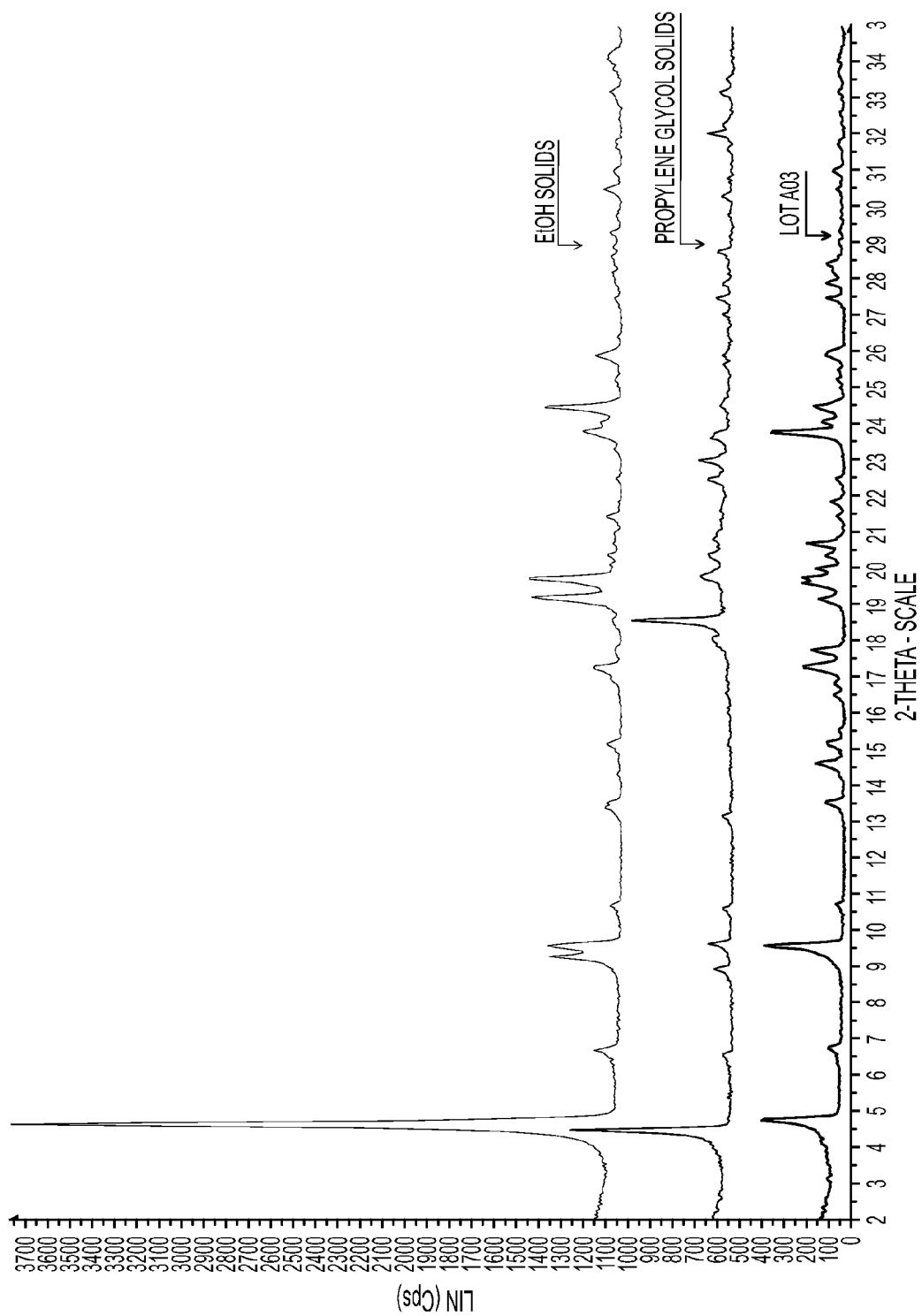
FIG. 5 shows the XRPD patterns of the Type A crystalline form of Compound (1) (bottom); the Type A crystalline form of Compound (1) after being slurried in propylene glycol (middle); and the Type A crystalline form of Compound (1) after being slurried in ethanol (top).

Second, the sodium salt unexpectedly exhibits higher form stability in propylene glycol and ethanol as compared to the Type A form. In particular, the Type A form of Compound (1) exhibits a clear form change when it is slurried in either ethanol or propylene glycol, as is demonstrated by a change in its XRPD pattern. FIG. 5 shows the XRPD patterns of the Type A crystalline form (bottom—Lot A03); the Type A form after being slurried in propylene glycol (middle—propylene glycol solids); and after being slurried in ethanol (top—EtOH solids), clearly showing the crystalline form changes. By contrast, when the crystalline sodium salt form of Compound (1) is slurried in either propylene glycol or ethanol, there is no change in the XRPD pattern observed for the remaining solid phase. This demonstrates the improved stability of the sodium salt form in these excipients which, again, makes the sodium salt form particularly suited to the development of an LBDDS formulation employing one or more of these common excipients. The methods used in generating these results are described below in the Methods of Characterization section.

The above results obtained with the crystalline sodium salt are unexpected because it is generally not possible to predict such differences in solubility and any trend in physical stability between the free form and different salt forms of a compound, and in particular for Compound (1), even after such forms have been successfully prepared.

In one general embodiment, the present invention is directed to the sodium salt of Compound (1).

In a more specific embodiment, the sodium salt of Compound (1) is in crystalline form.

In an even more specific embodiment, the present invention is directed to a crystalline sodium salt of Compound (1) that has at least the following characteristic: an X-ray powder diffraction pattern comprising a peak at 10.1 degrees 2θ (±0.2 degrees 2θ) when measured using CuKα radiation.

Another embodiment is directed to the crystalline sodium salt of Compound (1) having an XRPD pattern comprising a peak at 10.1 degrees 2θ (±0.2 degrees 2θ) as described above and further comprising peaks at 13.0 and 18.2 degrees 2θ (±0.2 degrees 2θ) when measured using CuKα radiation.

Another embodiment is directed to the crystalline sodium salt of Compound (1) having an XRPD pattern comprising a peak at 10.1 degrees 2θ (±0.2 degrees 2θ) as described above and further comprising peaks at 5.4, 8.7, 13.0 and 18.2 degrees 2θ (±0.2 degrees 2θ) when measured using CuKα radiation.

Another embodiment is directed to the crystalline sodium salt of Compound (1) having an XRPD pattern comprising a peak at 10.1 degrees 2θ (±0.2 degrees 2θ) as described above and further comprising peaks at 5.4, 6.5, 8.7, 11.9, 13.0, 18.2, 20.2 and 24.7 degrees 2θ (±0.2 degrees 2θ) when measured using CuKα radiation.

Another embodiment is directed to the crystalline sodium salt of Compound (1) exhibiting an XRPD pattern substantially the same as that shown in FIG. 3.

Another embodiment is directed to the crystalline sodium salt of Compound (1) having an XRPD pattern with a characteristic peak at 10.1 degrees 2θ (±0.2 degrees 2θ) as described above and also exhibiting a DSC thermal curve substantially the same as that shown in FIG. 4 at a heating rate of 10° C. per minute in an open cup.

Another embodiment is directed to a quantity of Compound (1) wherein at least 50%, preferably at least 75%, more preferably at least 95%, more preferably at least 99%, of said substance is present in the form of the crystalline sodium salt of Compound (1) as may be characterized by any of the abovementioned XRPD-defined embodiments. The presence of such amounts of crystalline sodium salt of Compound (1) in a quantity of Compound (1) is typically measurable using XRPD analysis of the compound.

An additional embodiment is directed to a pharmaceutical composition comprising Compound (1) sodium salt and a pharmaceutically acceptable carrier or diluent. In a more specific embodiment, at least 50%, preferably at least 75%, more preferably at least 95%, more preferably at least 99%, of the Compound (1) sodium salt in the composition is present in crystalline form, for example, in the form of a crystalline sodium salt of Compound (1) as may be characterized by any of the abovementioned XRPD-defined embodiments.

The present invention provides a process for the preparation of crystalline sodium salt of Compound (1) which comprises crystallizing Compound (1) from a solution in solvents under conditions which yield crystalline sodium salt. The precise conditions under which crystalline sodium salt is formed may be empirically determined and it is only possible to give methods which have been found to be suitable in practice.

It has been found that the crystalline sodium salt of Compound (1) may be prepared by a process comprising the following steps, which process is also an embodiment of the present invention:

(i) dissolving compound (1) in an ketones or acetate solvents, optionally containing water as a co-solvent, by heating the mixture as a slurry or by obtaining a complete solution (ii) adding water to the solution obtained in step (i) while maintaining the solution at a temperature of about 50-70° C. to obtain a solution or slurry;

(iii) seeding with the crystalline sodium salt of Compound (1)

(iv) cooling the slurry obtained in step (iii) to obtain solid material;

(iv) collecting the solid material of step (iii) and drying said material at a temperature of about 45 to 75° C. to obtain the crystalline sodium salt of Compound (1).

Additional alternative processes for preparing the crystalline sodium salt of Compound (1) may be found in the Examples section below, each of which are additional embodiments of the present invention.

Pharmaceutical Compositions and Methods

The aforementioned forms of Compound (1), including Type A and the sodium salt forms, are useful as anti-HCV agents in view of the demonstrated inhibitory activity of Compound (1) against HCV NS3 serine protease. These forms are therefore useful in treatment of HCV infection in a mammal and can be used for the preparation of a pharmaceutical composition for treating an HCV infection or alleviating one or more symptoms thereof in a patient. In addition, the sodium salt form of Compound (1) has demonstrated effectiveness in treating HCV-infected patients in human clinical trials. The appropriate dosage amounts and regimens for a particular patient can be determined by methods known in the art and by reference to the disclosure in U.S. Pat. Nos. 6,323,180 and 7,585,845. Generally, a therapeutically effective amount for the treatment of HCV infection in the mammal is administered. In one embodiment, about 50 mg to 1000 mg, more preferably from about 120 mg to about 480 mg, is administered per adult human per day in single or multiple doses.

Specific optimal dosage and treatment regimens for any particular patient will of course depend upon a variety of factors, including the age, body weight, general health status, sex, diet, time of administration, rate of excretion, drug combination, the severity and course of the infection, the patient's disposition to the infection and the judgment of the treating physician. In general, the compound is most desirably administered at a concentration level that will generally afford antivirally effective results without causing any harmful or deleterious side effects.

These crystalline forms of Compound (1) or the sodium salt thereof at a selected dosage level is typically administered to the patient via a pharmaceutical composition. See, e.g., the descriptions in U.S. Pat. Nos. 6,323,180 and 7,585,845 for the various types of compositions that may be employed in the present invention. The pharmaceutical composition may be administered orally, parenterally or via an implanted reservoir. The term parenteral as used herein includes subcutaneous, intracutaneous, intravenous, intramuscular, intra-articular, intrasynovial, intrasternal, intrathecal, and intralesional injection or infusion techniques. Oral administration or administration by injection are preferred.

The pharmaceutical compositions of this invention may contain any conventional non-toxic pharmaceutically-acceptable carriers, diluents, adjuvants, excipients or vehicles. In some cases, the pH of the formulation may be adjusted with pharmaceutically acceptable acids, bases or buffers to enhance the stability of the formulated compound or its delivery form.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example. Tween 80) and suspending agents.

The pharmaceutical compositions may also be in the form of an oral pharmaceutical composition comprising Type A or the sodium salt of Compound (1), or mixtures thereof, and at least one pharmaceutically acceptable carrier or diluent. The oral pharmaceutical compositions may be orally administered in any orally acceptable dosage form including, but not limited to, tablets, capsules (e.g., hard or soft gelatin capsules), including liquid-filled capsules, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. Examples of soft gelatin capsules that can be used include those disclosed in EP 649651 B1 and U.S. Pat. No. 5,985,321. When aqueous suspensions are administered orally, the active ingredient is combined with emulsifying and suspending agents. If desired, certain sweetening and/or flavoring and/or coloring agents may be added.

Other suitable vehicles or carriers for the above noted formulations and compositions can be found in standard pharmaceutical texts, e.g. in "Remington's Pharmaceutical Sciences", 19$^{th}$ ed., Mack Publishing Company, Easton, Pa., 1995.

Certainly, when the crystalline sodium salt is formulated in a liquid vehicle, for example, as a liquid solution or suspension for oral administration or by injection, including for example in liquid-filled capsules, the sodium salt loses its crystalline nature. Nevertheless, the final liquid-based pharmaceutical composition contains the novel sodium salt of Compound (1) and it is therefore to be considered a separate embodiment embraced by the present invention. It was only by discovering a method for preparing the sodium salt in a stable crystalline form that the present inventors enabled efficient pharmaceutical processing and pharmaceutical formulation manufacture using the sodium salt form. Therefore, the final pharmaceutical formulation containing the sodium salt form which was thereby enabled by this discovery is considered another aspect and embodiment of the present invention.

Methods of Characterization
1. X-Ray Powder Diffraction

X-ray powder diffraction analyses were conducted on a Bruker AXS X-Ray Powder Diffractometer Model D8 Discover, available from Bruker AXS, Inc. of Madison, Wis., using CuKα radiation. The instrument is equipped with a long fine focus x-ray tube. The tube power was set to 40 kV and 40 mA. The instrument was operated in parallel beam mode with a Gobel Mirror, using a 0.6 mm exit slit, a 0.4° soller slit, a LiF flat crystal diffracted beam monochromator and a NaI scintillation detector. A detector scan was run using a tube angle of 1° 2θ. Step scans were run from 2 to 40° 2θ, at 0.05° per step, 4 sec per step. A reference quartz standard was used to check instrument alignment. Samples were prepared for analysis by filing a zero background quartz holder.

2. DSC Analysis

The DSC analysis was conducted on a TA instruments DSC Q 1000. The differential scanning calorimetry curve was obtained on a sample of Type heated at 10 degrees C. in a crimped cup under a nitrogen flow.

3. Solubility and Form Change Studies

The solubility of Compound (1), as either Type A or the sodium salt form, was investigated in various non-aqueous solvents. The solutions were prepared by addition of excess Compound (1) to 0.25 ml to 1.0 ml of excipient in amber screw cap vials with Teflon lined caps. The samples were allowed to rotate at room temperature for up to 4 days. Sampling was done by centrifuging (14,000 rpm on the Eppendorf model 5415C table top centrifuge) and filtering through a 0.45 μm PVDF filter. The filtrate was subject to HPLC analysis for determining the solubility. HPLC analysis was conducted with an to Agilent 1100 using gradient or isocratic conditions. Both methods used acetonitrile/water (each with 0.1% Triflouroacetic Acid) and an ACE C-18 stationary phase with column heating maintained at 40-45° C. The wavelength of detection was set at 220 nm or 264 nm Wet solids were collected and analyzed for form change (stability) by XRPD.

XRPD analyses for the form change studies were conducted on a Bruker AXS X-Ray Powder Diffractometer Model D8 Discover or D8 Advance, available from Bruker AXS, Inc. of Madison, Wis., using CuKα radiation. The tube power was set to either 40 kV and 40 mA or 40 kV and 30 mA. The instrument(s) were operated in parallel beam mode with a Gobel Mirror, using a 0.6 mm exit slit with a 0.4° soller slit and LiF flat crystal diffracted beam monochromator or using 1 mm divergence slit with 0.12 mm soller slits. Bragg-Brentano configuration with the D8 Advance was also used for some analyses with 1 mm divergence slit with 0.12 mm soller slits. Each configuration/instrument employed NaI scintillation detector. Detector scans were run using a tube angle of 1° 2θ. Step scans were run from 2 to 35° or 40° 2θ, at 0.05° per step, with 0.6 or 4 seconds per step. A reference quartz standard was used to check instrument alignment. Samples were prepared for analysis by filing a zero background quartz holder or Ni plated holder.

In order that this invention be more fully understood, the following examples are set forth. These examples are for the purpose of illustrating embodiments of this invention, and are not to be construed as limiting the scope of the invention in any way. The reactants used in the examples below may be obtained either as described herein, or if not described herein, are themselves either commercially available or may be prepared from commercially available materials by methods known in the art. Certain starting materials, for example, may be obtained by methods described in the International Patent Applications WO 00/09543, WO 00/09558, WO 00/59929, U.S. Pat. Nos. 6,323,180, 6,608,027, 7,514,557 and 7,585,845.

Unless otherwise specified, solvents, temperatures, pressures, and other reaction conditions may be readily selected by one of ordinary skill in the art. Typically, reaction progress may be monitored by High Pressure Liquid Chromatography (HPLC), if desired, and intermediates and products may be purified by chromatography on silica gel and/or by recrystallization.

EXAMPLES

Example 1

Preparation of Quinoline Starting Material Compound 11

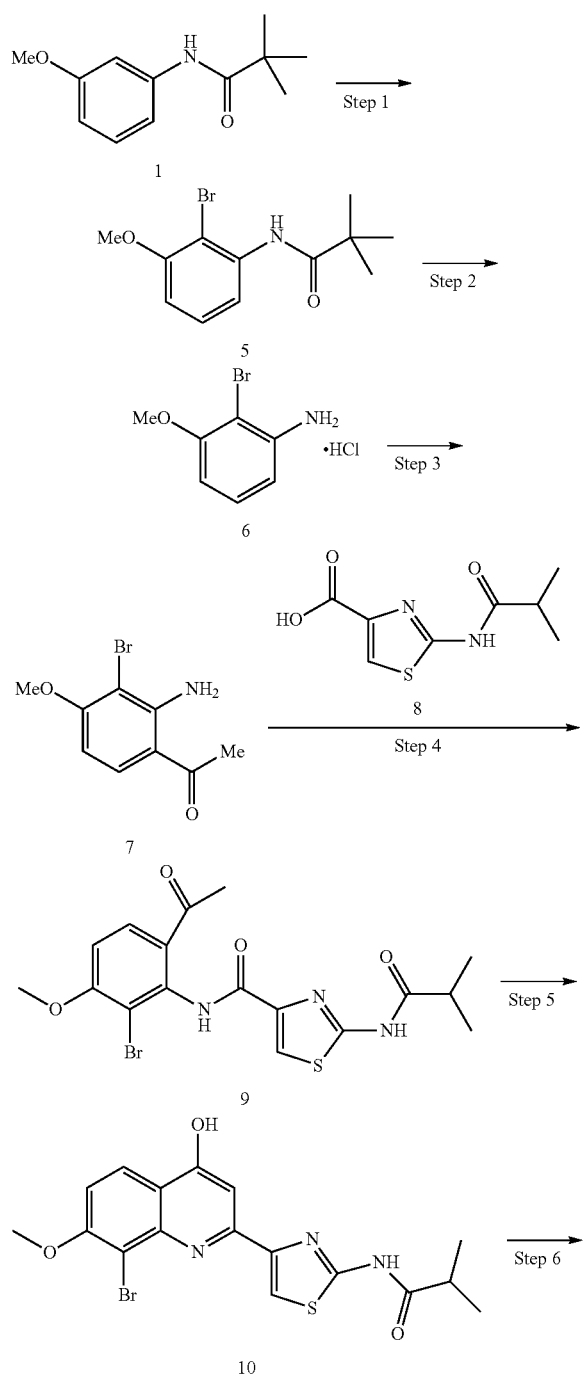

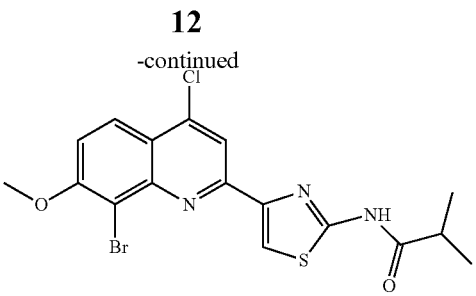

Step 1

The dianion of amide 1 (prepared exactly as described above, from 1.00 g amide 1) was cooled to −78° C., then 2.19 mL perfluorooctyl bromide (8.46 mmol, 1.75 eq.) was added dropwise via syringe over 5 minutes. The dark-colored reaction mixture was then placed in a −10° C. bath. After two hours, 10 mL 1N HCl was cautiously added, and the mixture extracted with EtOAc (2×25 mL), dried (MgSO$_4$), and the solvents removed in vacuo. The residue was then chromatographed on silica gel eluting with 4:1 Hexane:EtOAc to give 1.13 g bromoamide 5 (81%) as a colorless oil. $^1$H NMR (400 MHz, CDCl$_3$) δ: 8.12 (br s, 1H), 8.04 (dd, J=1.3, 8.4 Hz, 1H), 7.24 (t, J=8.3 Hz, 1H), 6.63 (dd, J=1.3, 8.3 Hz, 1H), 3.87 (s, 3H), 1.33 (s, 9H). $^{13}$C NMR (100 MHz, CDCl$_3$) δ: 176.57 (s), 155.74 (s), 136.98 (s), 128.34 (d), 113.63 (d), 106.86 (d), 103.07 (s), 56.26 (q), 40.20 (s), 27.45 (q).

Step 2

0.25 g bromoamide 5 (0.87 mmol, 1 eq.), 2.0 mL con. HCl (24 mmol, 28 eq.), and 1.0 mL diglyme were heated at 100° C. for 24 hours. The mixture was then cooled and filtered (product). The filtrate was evaporated in vacuo using H$_2$O to azeotropically remove all solvents. The residue was triturated with EtOAc to cause precipitation of additional product, which was also filtered. The combined solids were dried to give 0.16 g (77%) of bromoaniline 6.HCl as a light brown solid. $^1$H NMR (400 MHz, CDCl$_3$) δ: 7.09 (t, J=8.1 Hz, 1H), 6.61 (d, J=8.0 Hz, 1H), 6.47 (d, J=8.1 Hz, 1H), 3.84 (br s, 2H), 3.77 (s, 3H).

Step 3

Bromoanisidine.HCl (5.73 g, 24.0 mmol), Aluminumtrichloride (3.52 g) and chlorobenzene (15.0 mL) are charged into an oven dried 100 mL three necked flask at rt (temperature rise to 30° C.). The resulting mixture is then stirred for 10 min then cooled to 0-5° C. followed by slow addition of acetonitrile (1.89 mL, 36.0 mmol) followed by addition of BCl$_3$ (2.82 g), transferred as gas (or liquid) into the reaction mixture, keeping the temperature below 5° C. The resulting mixture is then stirred at rt for 20 min then heated to 85-100° C. for 16 h. HPLC indicate completion of the reaction (SM<0.5% at 220 nm). The mixture is cooled down to 50° C. then Toluene (15 mL) was added followed by slow addition of IPA (11.1 mL) then slow addition of water (32 mL) at 50° C. The resulting mixture stirred for additional 2 h at this temperature then 3 g Celite was added and the stirred mixture cooled to rt. Filtration then wash of the organic fraction with water 1×15 mL, 2×15 m: 5% NaHCO$_3$, 1×15 mL water then concentration under reduced pressure provided 3.92-4.4 g of the desired product in 68-72% isolated yield. $^1$H NMR (400 MHz, CDCl$_3$) δ: 7.72 (d, J=9.0 Hz, 1H), 7.1 (br s, 2H), 6.28 (d, J=9.1 Hz, 1H), 3.94 (s, 3H), 2.55 (s, 3H).

Step 4

Oxalyl chloride (8.15 mL) is added dropwise to the cold mixture (10±5° C.) of Thiazole acid 8 (20.18 g) is dissolved in THF (300 mL) and DMF (300 μL) over a period of ~5 min keeping the internal temperature at 10±5° C. The reaction mixture becomes yellow and homogenous. The cooling bath is removed and the mixture is allowed to reach ambient temperature over a period of ~30 min. Gas evolution is observed. The mixture is stirred at ambient temperature for 30 min to 1 hour. A solution of aniline 7 (19.8 g), DMAP (140 mg) and THF (35 mL) was added at 10±5° C. Et₃N (13.2 mL) was added in portions at 10±5° C. over a period of 10 min. The ice bath was removed and mixture was heated to 65±2° C. and stirred overnight (18 h). The mixture was allowed to reach ambient temperature, diluted with EtOAc (150 mL) and washed with water (150 mL). NaHCO₃ (5%, 225 mL) was added to the organic portion and the mixture was stirred at ambient temperature for 30 min. The organic portion was concentrated under reduced pressure at approx. 40° C. EtOAc (150 mL) was added to the resulting material and the residual water was removed and the mixture was concentrated under reduced pressure at approx. 40° C. (to azeotrope water). EtOAc (94 mL) was added and the resulting slurry was stirred for 2-6 h and filtered. The solid was washed with EtOAc (30 mL) followed by heptane (30 mL) and air dried for 1 h to give the desired product in 70% yield.

¹H NMR (400 MHz, CDCl₃) δ: 1.32 (d, 6H, J=7.8 Hz), 2.58 (s, 3H), 2.65-2.72 (m, 1H), 3.98 (s, 3H), 6.83 (d, 1H, J=8.7 Hz), 7.70 (d, 1H, J=8.7 Hz), 7.86 (s, 1H), 8.98 (bs, 1H), 10.13 (bs, 1H).

Step 5

In a 2 L flask was placed potassium t-butoxide (112 g). Dry DME was added at room temperature (exothermic: temperature went up to 35° C.). The resultant solution was heated to ca. 80° C., and amide (88 g) was added in 10 portions slowly so temperature was kept between 80-85° C. Upon completion, reaction mixture was stirred at 85° C. for 2 hours. Solid precipitated during the reaction. HPLC analysis indicated that the reaction was completed at this point (conversion: 100%). The reaction mixture was cooled to room temperature and then to 10° C. with a cool bath. Aqueous 2N HCl solution (ca. 500 ml) was added slowly so temperature was kept under 25° C. to quench the reaction mixture. pH was adjusted to 4-5. About 100 ml of water was added (Note: amount of water may need adjustment to facilitate filtration), and the resulting suspension was stirred at room temperature for 5-10 hours. Product was isolated by filtration, washing with THF and drying under vacuum. Yield: 81 g, 96% yield.

¹H-NMR (400 M Hz, DMSO-d₆): 1.14 (6H, d, J=6.8 Hz, i-Pr), 2.48 (1H, hept., J=6.8 Hz, i-Pr), 3.99 (3H, s, MeO), 6.75 (1H, s, H-3), 7.24 (1H, d, J=8.5 Hz, H-6), 8.10 (1H, d, J=8.5 Hz, H5), 8.22 (1H, s, H-5'), 9.87 (1H, s, OH), 12.40 (1H, s, amide NH).

Step 6

In a 100 ml flask was placed starting material quinolone (4.22 g) and dioxane (40 ml). POCl₃ (4.6 g) was added, and the mixture was heated to 75° C. After 2 hours, HPLC showed the reaction finished (99.7% conversion). Reaction mixture was cooled to room temperature, and then poured to 100 ml saturated NaHCO₃ solution and 20 ml EtOAc. The resulting suspension was stirred for 3 hours. Product was isolated by filtration, washing with EtOAc and drying under vacuum. Yield: 4.0 g, 90.9%.

¹H-NMR (400 M Hz, CDCl₃): 1.14 (6H, d, J=6.8 Hz, i-Pr), 2.76 (1H, hept., J=6.8 Hz, i-Pr), 4.05 (3H, s, MeO), 7.68 (1H, d, J=8.5 Hz, H-6), 8.07 (1H, s, H-3), 8.13 (1H, s, H-5'), 8.20 (1H, d, J=8.5 Hz, H5), 12.30 (1H, s, amide NH).

Example 2

Preparation of Dipeptide Acid Compound 13 Starting Material

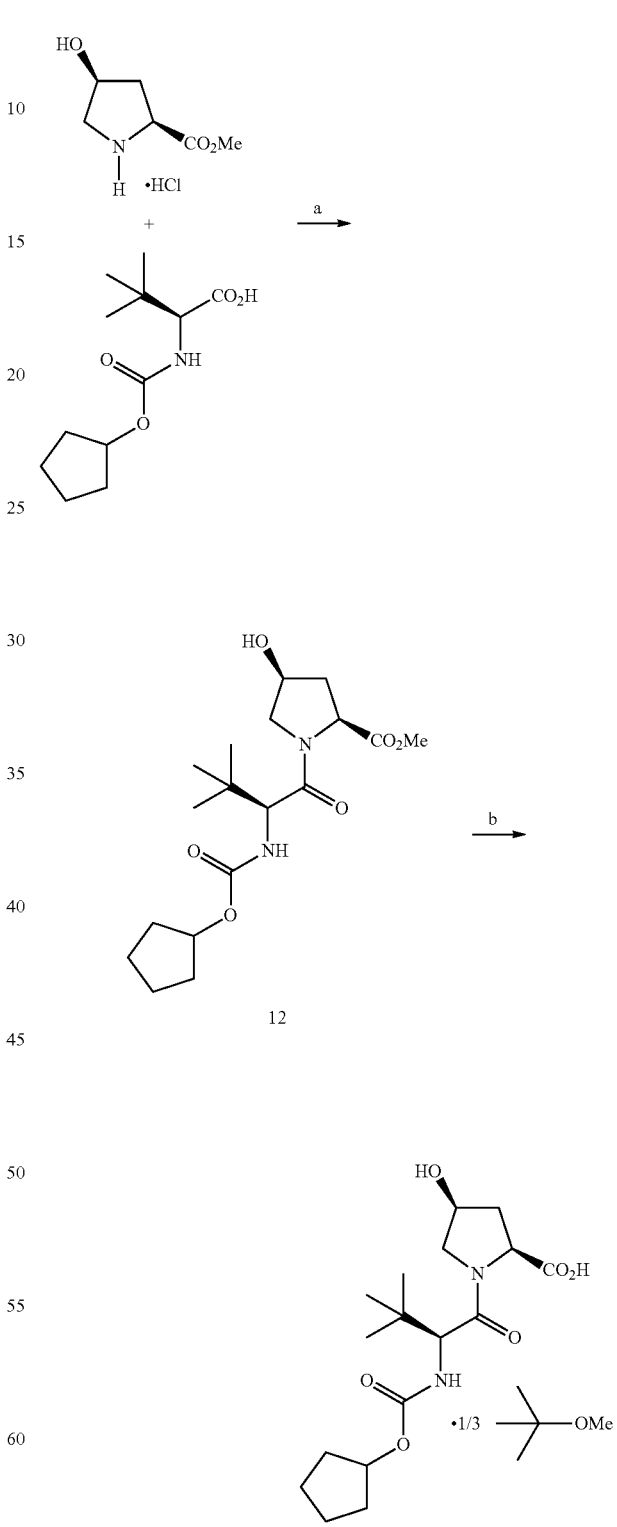

a) EDC, HOBT, DMF, DIEA, 90%
b) i) LiOH, H₂O, THF, MeOH ii) MTBE recrystallization A 250 mL 3-neck flask with a thermocouple, nitrogen inlet, and magnetic stir bar was charged with N-cyclopentlyoxy carbonyl-tert-L-leucine (20.0 g, 82.2 mmol, 1.0 eq.), 1-hydroxy-benzotriazole (12.73 g, 90.42 mmol, 1.1 eq), and 1-(3-dimethylaminopropyl)-3-ethylcarbodiimide hydrochloride (17.33 g, 90.42 mmol, 1.1 eq.) The flask was purged with nitrogen, and the stiffing started. Anhydrous DMF (62 mL) was added to the flask and the mixture was stirred for 20 minutes at room temperature (about 24° C.). The reaction was mildly exothermic, the internal temperature rose to 29° C. Solid trans-4-hydroxyproline methyl ester HCl (14.93 g, 82.2 mmol, 1.0 eq) was added to the reaction in one portion. Using a syringe, diisopropyl ethyl amine (14.36 mL, 82.2 mmol, 1.0 eq) was added to the reaction dropwise over 25 min. The internal temperature rose to 34.5° C. from 29° C. The reaction was stirred for 1.75 h, forming 12. The reaction was then quenched with 0.1 M HCl (100 mL), the internal temperature rose to 34° C. The reaction was extracted three times with 75 mL of ethyl acetate, and the organic layers were combined. The organic layer was washed with 75 mL H$_2$O, and 2×75 mL of sat. NaHCO$_3$. The organic layer (about 235 mL) was transferred to a 500 mL flask fitted with a mechanical stirrer, shortpath distillation head, internal and external thermocouples, and distilled to minimal stirrable volume under house vacuum (~110 mm Hg,) below 35° C. internal temperature with an oil bath temperature of 40° C. To this crude mixture of 12 was then added tetrahydrofuran (150 mL) and it was distilled to minimum stirrable volume. Tetrahydrofuran (100 mL) was added to the flask, and it was again distilled to minimum stirrable volume. The distillation head was replaced with an addition funnel. Tetrahydrofuran, (100 mL) and methanol (50 mL) were added to the flask, and the solution stirred for about 15 minutes. A 3.2 M solution of LiOH (77 mL, 246.6 mmol, 3 eq.) was charged to the addition funnel, and added over 45 minutes. The temperature rose from 22° C. to 29° C., and the reaction mixture became slightly cloudy. The mixture was cooled in a cold water bath, then the reaction was quenched by slow (45 min.) addition of 4 M HCl (58-65 mL) to adjust the pH to 3.5, causing a slight increase in temperature to 27° C. The flask was fitted with a distillation head, and the methanol and tertahydrofuran were removed by distillation at reduced pressure, with a bath temperature of 40° C., internal temperature below 30° C. The mixture was extracted twice with 150 mL of MTBE. The MTBE solution was concentrated at reduced pressure, (350 mmHg) to minimum stirrable volume. 50 mL of MTBE was added, it was removed by distillation, internal temp below 35° C. The reaction was a clear viscous liquid, 20 mL of MTBE was added, the mixture was heated to 50° C., solution was clear, the oil bath was turned off, and the solution cooled to rt, ~24° C. over 1.5 h. To the resultant slurry was then added 60 mL MTBE, stirred 2 h, then the slurry was filtered, using ~20 mL MTBE to transfer the mixture. The solid was then dried under vacuum at 35° C. to constant weight, 16.4 g (52%), to give the ⅓ MTBE solvate compound 13 as a colorless solid, m.p. 117-124° C.; α$_D$=−58.6 (c 2.17, MeOH); $^1$H NMR (400 MHz, DMSO, major rotamer reported) δ: 6.76 (d, J=9.3 Hz, 1H), 5.15 (s, 1H), 4.92 (m, 1H), 4.31 (br s, 1H), 4.26 (t, J=8.3 Hz, 1H), 4.19 (d, J=9.3 Hz, 1H), 3.63 (m, 2H), 3.06 (s, 1H (MTBE)), 2.08 (m, 1H), 1.87-1.48 (m, 9H), 1.09 (s, 3H, (MTBE)), 0.92 (s, 9H).

Example 3

Preparation of Tripeptide Acid Compound 16 Starting Material

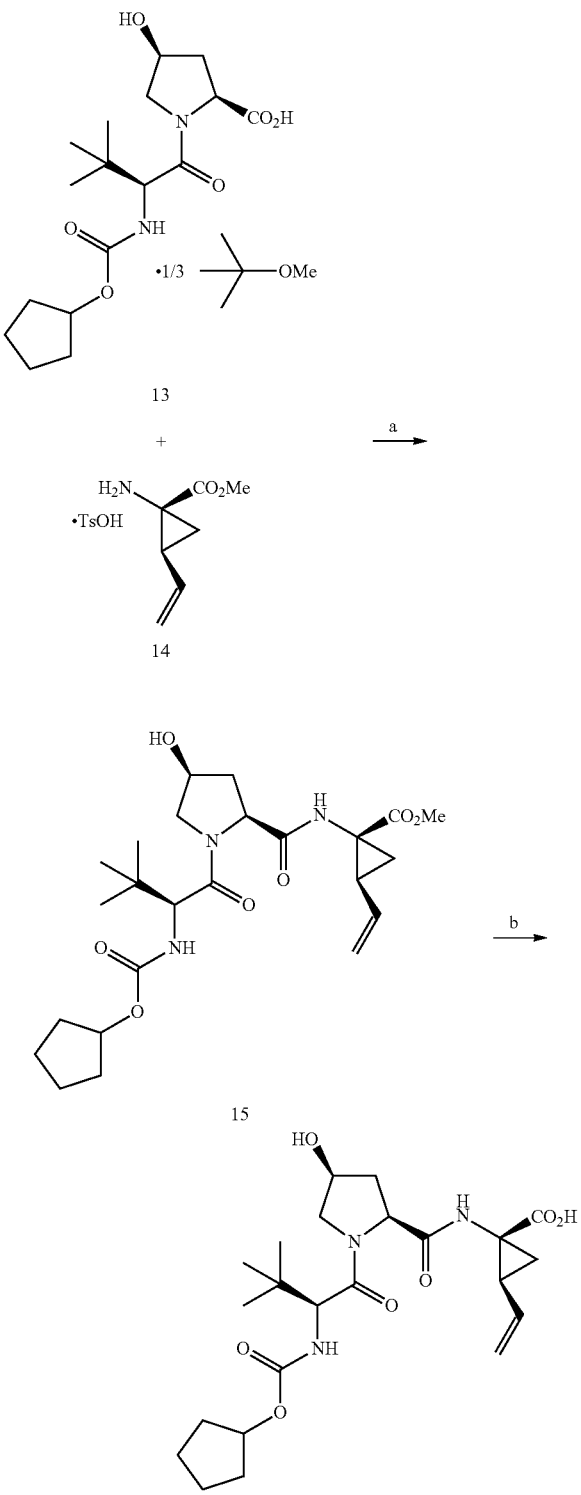

a) EDC, HOBT, THF
b) LiOH, H$_2$O, THF, MeOH

In a 25 ml flask 14 was dissolved in 3 ml DMF. HOBt (149 mg, 1.1 mmol), EDC (211 mg, 1.1 mmol), 13 (290 mg, 1.0 mmol) and i-Pr$_2$NEt (129 mg, 1.0 mmol) were added in the given order at room temperature. The resulting reaction mixture was stirred at room temperature overnight. The reaction mixture was poured into 15 ml aqueous NaHCO$_3$ and extracted with ethyl acetate (20 ml). The organic layer was washed with HCl (0.5 N, 2×10 ml) and saturated aqueous NaHCO$_3$ (10 ml). After removal of solvent by rotary evaporation, 15 was obtained as a white solid. 0.46 g (95% yield). $^1$H-NMR (400 M Hz, CDCl$_3$): 0.96 (s, 9H), 1.35 (1H, dd, J=3.0, 4.5 Hz), 1.45-1.90 (m, 9H), 1.77 (1H, dd, J=3.0, 4.0 Hz), 2.00-2.09 (1H, m), 2.45-2.52 (1H, m), 3.02 (1H, br), 3.50 (1H, dd, J=11.0, 3.0 Hz), 3.58 (3H, s), 3.99 (1H, d, J=11.0 Hz), 4.18 (1H, d, J=9.0 Hz), 4.43 (1H, br), Hz), 4.63 (1H, t, J=8.0 Hz), 4.93-5.00 (1H, m), 5.04 (1H, dd, J=10.5, 2.0 Hz), 5.20 (1H, d, J=18.0 Hz), 5.20-5.25 (1H, m), 5.65-5.77 (1H, ddd, J=18.0, 10.5, 2.0 Hz), 7.78 (1H, br) ppm.

320 mg ester 15 (0.667 mmol, 1 eq.) was dissolved in 6.7 mL THF+3.4 mL MeOH at ambient temperature under N$_2$. To this solution was then added 3.34 mL 1.6 M LiOH (5.34 mmol, 8 eq.) dropwise over 5 minutes. After 1.5 hours, the solvents were removed in vacuo, and the residue diluted with 15 mL EtOAc+10 mL sat'd NaCl then 1N HCl was added until pH 3.45 was reached. The phases were separated and the aqueous phase reextracted with 15 mL EtOAc. The combined EtOAc layers were washed with H$_2$O (1×50 mL), dried (MgSO$_4$), and the solvents removed in vacuo to give an oil. The oil was azeotroped with MTBE (1×15 mL), and the residue dried under high vacuum to give 320 mg of 16 (100%) as a colorless foam. Exact mass calc'd for C$_{23}$H$_{35}$N$_3$O$_7$: 465.25; Found (ES−): 464.29; $^1$H NMR (400 MHz, DMSO, major rotamer reported) δ: 12.40 (br s, 1H), 8.49 (s, 1H), 6.77 (d, J=8.2 Hz, 1H), 5.71 (m, 1H), 5.22-4.85 (m, 4H), 4.36-4.10 (m, 3H), 3.80-3.21 (m, 4H), 2.00-1.42 (m, 11H), 0.92 (s, 9H).

Example 4

Dipeptide S$_N$Ar Approach to amorphous Compound (1)

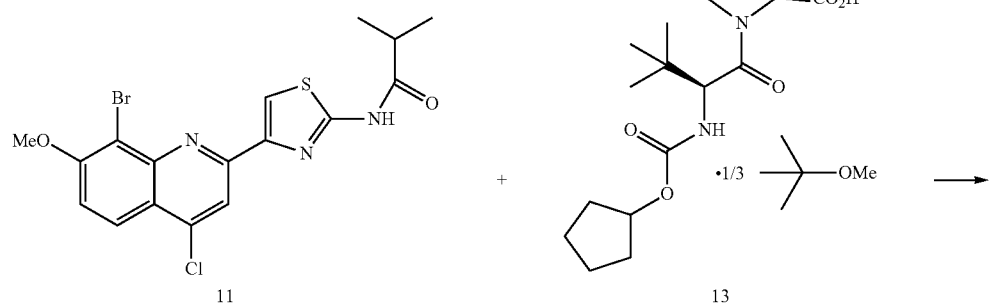

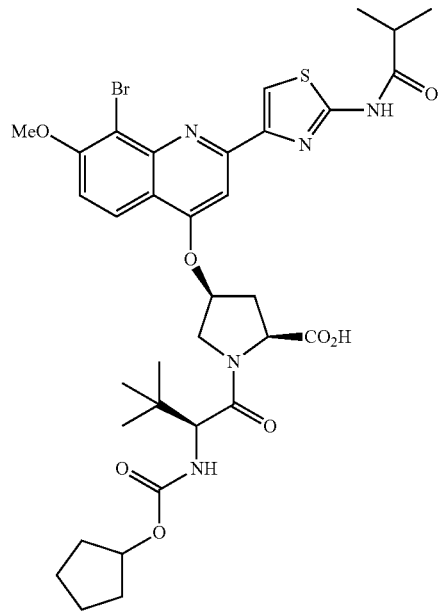

-continued

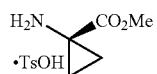

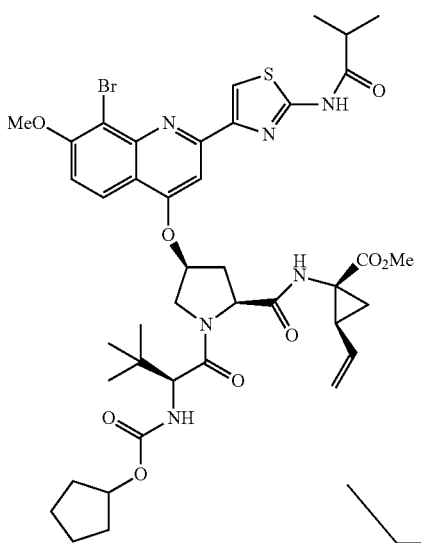

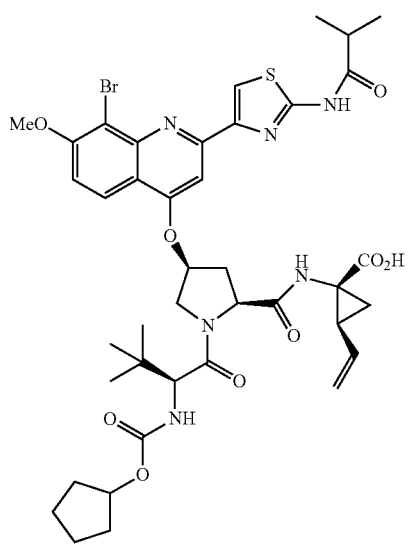

(1)

S$_N$Ar Protocol 1: A 100 mL 3-neck round bottom flask was charged with 1.93 g 13 (5.00 mmol, 1 eg.), then evacuated/Ar filled (3×), then 17.0 mL DMSO was added via syringe to give a clear, colorless solution. The flask was again evacuated/Ar filled (3×), then 2.53 g t-BuOK (22.5 mmol, 4.5 eq.) was added neat, at once. An exotherm to a maximum of 31.5° C. was observed. The flask was evacuated/Ar filled (3×), then stirred under house vacuum (~60 mm) for one hour, and some foaming (-t-BuOH) was observed. The vacuum was relieved to Ar, then 2.20 g 11 (5.00 mmol, 1 eq.) was added neat, at once. An exotherm to 28.6° C. was observed. The flask was evacuated/Ar filled (3×), then stirred under house vacuum protected from light at ambient temperature. After 6.5 h the vacuum was relieved to Ar and a sample removed for HPLC, which showed <2% unreacted 11. The flask was then cooled in a cold water bath to 18° C., and 1.72 mL glacial HOAc (30 mmol, 6 eq.) was then added via syringe over ~10 minutes. An exotherm to 20.5° C. was observed. The mixture was stirred for 10 minutes, then added dropwise over 15 minutes into a second flask containing a well-stirred solution of 30 mL pH 3.5 H$_2$O (~0.001 M HCl) at 18° C., causing a precipitate to form immediately, and giving an exotherm to 21.0° C. 2.0 mL DMSO was used to wash the residue into the aqueous mixture, followed by a wash of 5.0 mL ~0.001 M HCl. The resulting suspension was stirred for 15 minutes, then 30 mL of a 1:1 mixture of EtOAc:MTBE was added, and the mixture agitated vigorously for 15 minutes. Agitation was stopped and the phases were allowed to separate. Rapid phase separation and formation of 2 clear phases with no rag layer was seen. The lower aqueous phase was then reextracted with 30 mL of 1:1 EtOAc:MTBE (same fast separation), and the organic extracts were combined and saved. The aqueous phase was discarded as waste.

The organic solution was then washed with H$_2$O (3×30 mL), again all extractions gave rapid separation of phases and no rag layer, then the EtOAc was distilled to minimal stirrable volume. The residue was then azeotroped with 30 mL THF (2×), again distilling to minimal stirrable volume. The resultant slurry of crude 18 was used immediately in the peptide coupling. Exact mass calc'd for $C_{34}H_{42}BrN_5O_8S$: 759.19. Found (MS−): 757.92.

$S_NAr$ Protocol 2: 1.00 g 13 (2.59 mmol, 1 eq.) and 1.35 g 11 (2.59 mmol, 1 eq.) were charged to a dry flask. The flask was then evacuated/Ar filled (3×), then 10 mL dry DMSO was added via syringe. The flask was again evacuated/Ar filled (3×), then cooled to 19° C. with a cold water bath. To this mixture was then added a 2M solution of KDMO/heptane (5.71 mL, 11.7 mmol, 4.5 eq.) dropwise over 30 minutes. After six hours, HPLC showed the reaction as complete. The reaction was quenched with 0.89 mL HOAc (6 eq.), and added slowly to 25 mL stirring $H_2O$, causing a precipitate to form. The mixture was then extracted with IPAc (2×25 mL). The combined IPAc phases were washed with $H_2O$ (1×25 mL), dried ($MgSO_4$), and the solvents removed in vacuo to give a solid, which was azeotroped with MeCN (1×25 mL), and then diluted with heptane to give a slurry. The slurry was filtered and dried to give 1.80 g 18 (91%).

Peptide Coupling Protocol 1: To the THF slurry of crude 18 from $S_NAr$ Protocol 1 (taken as 5.00 mmol, 1 eq.) under Ar at ambient temperature in a flask protected from light was added 1.72 g 14 (5.5 mmol, 1.1 eq.) and 25 mL THF. The solution was then cooled to 5° C. under Ar, then 0.958 mL DIEA (5.50 mmol, 1.1 eq.) was added dropwise via syringe over 5 minutes. 5 minutes after the DIEA addition was completed, 0.85 g HOBT hydrate (6.00 mmol, 1.2 eq.), and 1.05 g EDC (5.50 mmol, 1.1 eq.) was then added neat, at once. The flask was then removed from the cold bath and the resultant mixture was then stirred at ambient temperature under Ar for 4 hours. A sample was withdrawn for HPLC which showed <2% unreacted 18 remained. The mixture was cooled to 5° C., then 40 mL 0.1N HCl was added dropwise via addition funnel over 5 minutes, followed by 40 mL EtOAc. The mixture was well agitated for 15 minutes, then agitation was stopped and the phases were allowed to separate. The lower aqueous phase was then reextracted with 40 mL EtOAc and the organic phases were combined and saved. The aqueous phase was discarded as waste. The organic solution was then washed with $H_2O$ (1×40 mL), sat'd $NaHCO_3$ (2×40 mL), and again $H_2O$ (1×40 mL), then distilled to minimal stirrable volume. The residue was then azeotroped with MTBE (2×40 mL), and again distilled to minimal stirrable volume. The residue was dried under high vacuum to give 4.70 g of crude 19 as an orange solid, with HPLC purity of 78.3%. This material was then chromatographed on silica gel eluting with 2:1 EtOAc:Hexane to give 3.01 g (68% over 2 steps) pure 19 as a yellow powder. Exact mass calc'd for $C_{41}H_{51}BrN_6O_9S$: 882.26, MS+: 883.30. $^1$H NMR (400 MHz, DMSO, major rotamer reported) δ: 12.32 (s, 1H), 8.69 (s, 1H), 8.14 (d, J=9.2 Hz, 1H), 8.03 (s, 1H), 7.45 (s, 1H), 7.33 (d, J=9.4 Hz, 1H), 6.97 (d, J=8.6 Hz, 1H), 5.65 (m, 1H), 5.40 (s, 1H), 5.20 (dd, J=1.5, 17 Hz, 1H), 5.06 (dd, J=1.6, 10.2 Hz, 1H), 5.56 (s, 1H), 4.46 (m, 1H), 4.37 (d, J=9 Hz, 1H), 4.08 (m, 1H), 3.99 (s, 3H), 3.90 (m, 1H), 3.56 (s, 3H), 2.81 (m, 1H), 2.51 (m, 1H), 2.25 (m, 1H), 2.07 (m, 1H), 1.70-1.32 (m, 7H), 1.30 (m, 3H), 1.15 (d, J=8.1 Hz, 6H), 0.95 (s, 9H).

Peptide Coupling Protocol 2: A 5 L 4-neck RBF fitted with mech. stirrer, addition funnel, and thermocouple was charged with 69.57 g 14 (222 mmol, 1.3 eq.), then evacuated/Ar filled (3×). To this was then added a 200 mL THF solution of 18 (contains 129.85 g 171 mmol, 1 eq.), then 523 mL THF was charged to bring the final THF volume to 1 L. The mixture was then cooled to 4.0° C. under Ar. 38.67 mL DIEA (222 mmol, 1.3 eq.) was then added dropwise via addition funnel over 10 minutes, as the internal temperature fell to 2.4° C. The mixture was aged 5 minutes, then 29.98 g HOBT $H_2O$ (222 mmol, 1.3 eq.) was added, followed by 42.57 g EDC (222 mmol, 1.3 eq.). The internal temperature was then 3.6° C. The bath was then removed. The internal temperature rose to 20.5° C. over 90 minutes. 4 h after the EDC addition was completed, HPLC showed the reaction was complete. The mixture was cooled to 4.0° C., then 750 mL 0.1N HCl was added over 30 minutes via addition funnel, giving an exotherm to 9.5° C. To this mixture was then added 250 mL sat'd NaCl, followed by 1 L IPAc. After 5 min. vigorous stirring, the mixture was added to a separatory funnel, and the phases were separated. The lower aq. phase was then reextracted with 500 mL IPAc, and the IPAc phases combined. These were then washed successively with $H_2O$ (1×1 L), sat'd $NaHCO_3$ (1×1 L), and then $H_2O$ (1×1 L). The mixture was then mech. stirred for 12 h to precipitate quinolone 7. The mixture was then filtered through a medium-fritted funnel, and the filtrate distilled until minimal stirrable volume was reached. The residue was then azeotroped with MTBE (2×400 mL), and again distilled to minimal stirrable volume. The residue was dried under high vacuum to give 128 g of 19 as a yellow solid, with HPLC purity of 89%.

140 mg 19 (0.158 mmol, 1 eq.) was dissolved in 1.6 mL THF+0.80 mL MeOH at ambient temperature under $N_2$. To this solution was then added 0.79 mL 1.6 M LiOH (1.27 mmol, 8 eq.) dropwise over 5 minutes. After 1.5 h, the organic solvents were removed in vacuo, and the residue diluted with 10 mL EtOAc+10 mL sat'd NaCl. The pH was then adjusted to 5.75 with 1N HCl. The mixture was agitated vigorously for one hour, then the phases were separated. The aqueous phase was reextracted with 10 mL EtOAc. The combined EtOAc phases were then washed with $H_2O$ (2×25 mL), dried ($MgSO_4$), and the solvents removed in vacuo to give 125 mg of Compound (1) (91%) as an amorphous yellow powder.

Example 5

Tripeptide $S_NAr$ Approach to amorphous Compound (1)

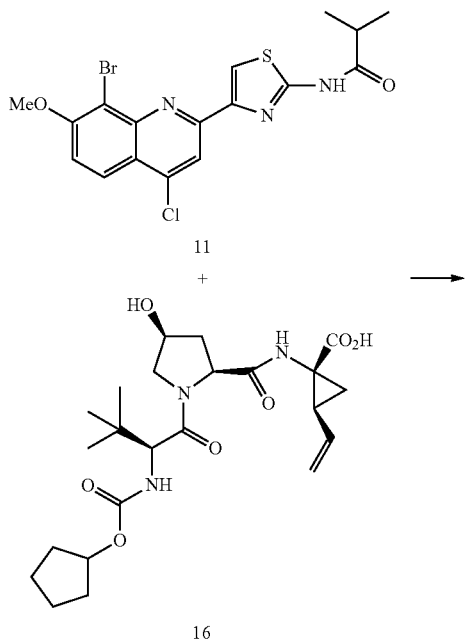

-continued

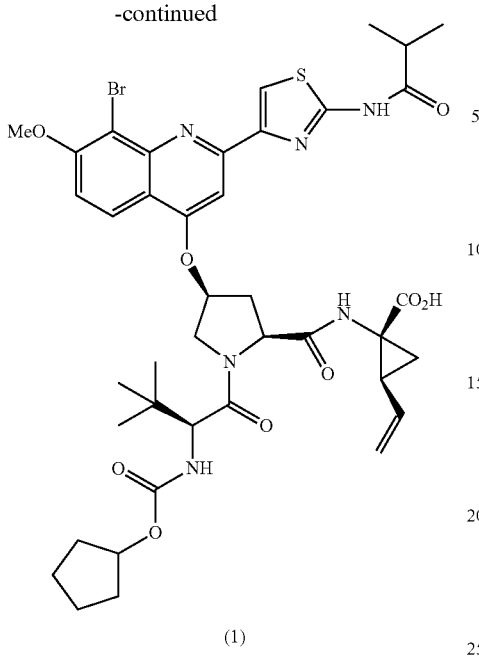

(1)

233 mg tripeptide acid 16 (0.50 mmol) was charged to a flask, then the flask was evacuated/Ar filled (3×). 1.7 mL DMSO was then added, and the mixture evacuated/Ar filled (3×). The mixture was then cooled in a cold water bath, then 317 mg t-BuOK (2.82 mmol, 5.63 eq.) were added. The flask was again evacuated/Ar filled (3×), then stirred under 60 mm vacuum for one hour. 220 mg quinoline 11 (0.50 mmol, 1 eq.) was then added, and the flask evacuated/Ar filled (3×), then stirred under 60 mm vacuum in the dark at ambient temperature for 3 hours. 0.30 mL HOAc was then added, then the resulting solution was added to 25 mL 0.001 M HCl, causing a precipitate to form. The slurry was filtered, washing the solids with 25 mL $H_2O$. The solid was dried under $N_2$ for 2 hours, then chromatographed on silica gel eluting with EtOAc to give 226 mg (52%) of Compound (1) as an amorphous yellow solid.

Additional methods for preparing amorphous Compound (1) can be found in U.S. Pat. Nos. 6,323,180, 7,514,557 and 7,585,845, which are herein incorporated by reference.

Example 6

Preparation of Type A of Compound (1)

Amorphous Compound (1) (Batch 7, 13.80 g) was added to a 1000 ml three neck flask. Absolute ethanol (248.9 g) was added to the flask. While stirring, the contents of the flask were heated at 60 degrees C/hr to ~74 degrees C. (Solids do not dissolve at 74 degrees C.). Water (257.4 g) was then added linearly over 4 hr to the resulting slurry while stirring and maintaining the temperature at 74 degrees C. After the water addition was complete, the temperature was reduced linearly to ambient temperature at 8 degrees C/hr and then held at ambient temperature for 6 hrs while stirring. The resulting solids were collected by filtration and washed with 50 ml of 1/1 (w/w) EtOH/Water. The wet solids were dried on the funnel for 30 minutes by sucking $N_2$ through the cake. (XRPD analysis on this sample indicates that the pattern is similar to the EtOH solvate). The solids were then dried at 65-70 degrees C. under vacuum (P=25 in Hg) and a nitrogen bleed for 1.5 hr. The resulting solids (12.6 g, 95.5% corrected yield) were confirmed by XRPD as being Type A Compound (1).

The unique XRPD pattern and DSC curve of Type A Compound (1) is shown in FIGS. 1 and 2.

Example 7

Preparation of the Sodium Salt of Compound (1)—Method 1

2.1 g of amorphous sodium salt of Compound (1) and 8.90 g of acetone was added to a vial and stirred at ambient temperature for 3 hr. The slurry was filtered off mother liquors and the resulting solids were dried for 20 minutes under nitrogen flow for 20 minutes. 1.51 g of crystalline sodium salt of Compound (1) as solids was collected.

Example 8

Preparation of the Sodium Salt of Compound (1)—Method 2

15.6 g of Type A of Compound (1), 175 ml of acetone and 3.6 ml of water was added to a 250 ml reactor and heated to 53 degrees C. to dissolve the solids. 900 ul of 10.0 N NaOH was added to reactor and the solution was seeded with Type A. The seeded solution was stirred at 53 degrees C. for 10 minutes. A second 900 ul portion of 10.0 N NaOH was added and the system was stirred at 53 degrees C. for 30 minutes over which a slurry developed. The slurry was cooled to 19 degrees C. at a cooling rate of 15 degrees C. per hour and held overnight at 19 degrees C. The final resulting slurry was filtered and the wet solids were washed with 15 ml of acetone. Dried solids for 1 hr at 52 degrees C. under vacuum with a nitrogen flow and then exposed the solids to lab air for one hour. Collected 12.1 g of Compound (1) crystalline sodium salt solids.

Example 9

Preparation of the Sodium Salt of Compound (1)—Method 3

25.4 Kg of amorphous Compound (1), 228 L of THF and 11.1 Kg of 10 wt % NaOH (aq) was added to a reactor. The components were mixed at 25 degrees C. to dissolve all solids. The resulting solution was filtered and the reactor and filter was washed with 23 L of THF. 180 L of solvent was removed using atmospheric distillation at 65 degrees C. 195 L of MIBK was added and 166 L of solvent was removed by vacuum distillation at ~44 degrees C. 161 L of MIBK and 0.41 Kg of water was added back to the reactor and the contents were heated to 70 degrees C. 255 g of Compound (1) sodium salt seeds were added at 70 degrees C. and 1.42 L of water was added over 1.5 hours. After the water addition the slurry was held at 70 degrees C. for 45 minutes and then cooled to 45 degrees C. over 1 hr. The resulting slurried was filtered and washed with 64 L of MIBK containing ~0.8 weight % water. The wet cake was dried at 55 degrees C. to give ~25 Kg of crystalline sodium salt of Compound (1).

Example 10

Preparation of the Sodium Salt of Compound (1)—Method 4

2.00 g of amorphous Compound (1), 9.96 g of THF and 0.11 g of water was added to a reactor and stirred at ambient temperature to dissolve solids. 0.820 ml of 21 weight % NaOEt in ethanol was added drop-wise while stirring the solution to get solution A. 15.9 g of n-BuAc and 160 ul of water was added to a second reactor and heated to 65 degrees C. (solution B). 2.56 g of Solution A was added to Solution B at 65 degrees C. and the resulting mixture was seeded with 40 mg of Compound (1) sodium salt seeds. The seeded mixture was aged at 65 degrees C. for 45 minutes. 2.56 g of Solution B was added to Solution A and aged for 45 minutes in four separate intervals. After the final addition and aging, the slurry was cooled to 50 degrees C. over 1 hour and filtered. The wet cake was washed with 6 ml of n-BuAc containing 0.5 weight % water. The final solids were dried at 50 degrees C. under vacuum using a nitrogen purge. Compound (1) crystalline sodium salt solids were collected.

Example 11

Preparation of the Sodium Salt of Compound (1)—Method 5

At room temperature a solution of sodium ethoxide in ethanol (21 weight %; 306 ml) was added to a solution of Compound (1) (745 g) in THF (2000 ml) and water (76.5 ml) while stirring. After stirring for 30 minutes, the mixture was filtered and the filter was washed with THF (85 ml). The resulting solution was warmed to 65° C. and treated with filtered butyl acetate (6640 ml, optionally pre-warmed to 65° C.) within 30 minutes. Seeding crystals (0.50 g) were added, and the mixture was stirred at 65° C. for 2 hours, while crystallization starts after about 30 minutes. The suspension was cooled to 50° C. within 1 hour and stirred at this temperature for an additional hour. The title compound was isolated by filtration, washed with filtered butyl acetate (765 ml, optionally pre-warmed to 50° C.) and dried at 65° C. for about 16 h giving Compound (1) crystalline sodium salt (~725 g).

The unique XRPD pattern and DSC curve of Compound (1) crystalline sodium salt is shown in FIGS. 3 and 4.

The invention claimed is:

1. A crystalline sodium salt of the compound of the following formula (1):

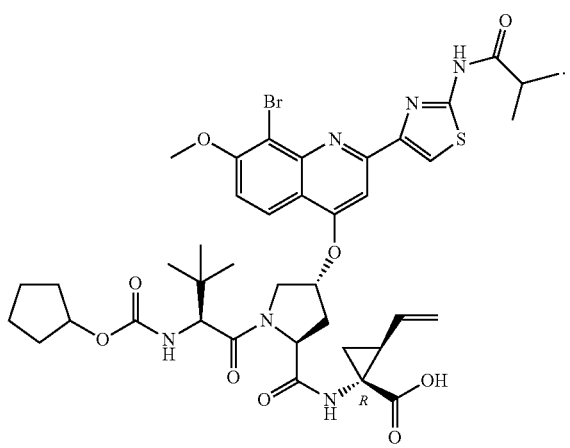

(1)

2. A pharmaceutical composition comprising the crystalline sodium salt of claim 1 and a pharmaceutically acceptable carrier or diluent.

3. A pharmaceutical composition prepared by combining a sodium salt of the compound of the following formula (1) in crystalline form:

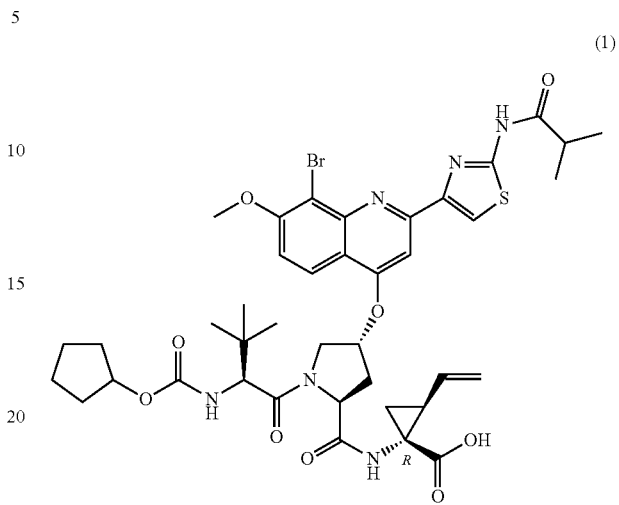

(1)

having an X-ray powder diffraction pattern comprising peaks at 10.1, 13.0 and 18.2 degrees 2θ (±0.2 degrees 2θ) when measured using CuKα radiation, with at least one pharmaceutically acceptable carrier or diluent, wherein the composition is in the form of a liquid solution, suspension or liquid-filled capsule.

4. The pharmaceutical composition according to claim 3, wherein the crystalline sodium salt has an X-ray powder diffraction pattern further comprises peaks at 5.4 and 8.7 degrees 2θ (±0.2 degrees 2θ) when measured using CuKα radiation.

5. The pharmaceutical composition according to claim 3, wherein the crystalline sodium salt has an X-ray powder diffraction pattern comprising peaks at 5.4, 6.5, 8.7, 10.1, 11.9, 13.0, 18.2, 20.2 and 24.7 degrees 2θ (±0.2 degrees 2θ) when measured using CuKα radiation.

6. A pharmaceutical composition prepared by combining the crystalline sodium salt of claim 1 with at least one pharmaceutically acceptable carrier or diluent.

7. A pharmaceutical composition according to claim 6, wherein the composition is in the form of a liquid solution, suspension or liquid-filled capsule.

8. A method of treating Hepatitis C viral infection in a mammal comprising administering to said mammal a therapeutically effective amount of the crystalline sodium salt according to claim 1.

9. A method of treating Hepatitis C viral infection in a mammal comprising:
 (a) preparing a pharmaceutical composition by a process comprising combining the crystalline sodium salt of claim 1, with at least one pharmaceutically acceptable carrier or diluent; and
 (b) administering to said mammal a therapeutically effective amount of the prepared pharmaceutical composition.

10. A method of treating Hepatitis C viral infection in a mammal comprising administering to said mammal a therapeutically effective amount of a pharmaceutical composition prepared by a process comprising combining the crystalline sodium salt of claim 1, with at least one pharmaceutically acceptable carrier or diluent.

* * * * *